United States Patent [19]

Steiner

[11] 4,059,422

[45] Nov. 22, 1977

[54] DISPENSER FOR ODOR CONTROL AGENT

[75] Inventor: Robert L. Steiner, Chicago, Ill.

[73] Assignee: Steiner American Corporation, Salt Lake City, Utah

[21] Appl. No.: 697,867

[22] Filed: June 21, 1976

[51] Int. Cl.$^2$ .............................. B01D 53/04
[52] U.S. Cl. ............................ 55/418; 21/126
[58] Field of Search ........... 55/471, 473, 74, 387, 55/279, 417, 418, 468–470, 481; 239/51.5, 55, 57; 21/126, 55

[56] References Cited

U.S. PATENT DOCUMENTS

| 2,114,761 | 4/1938 | Crider | 55/471 |
|---|---|---|---|
| 2,778,441 | 1/1957 | Herriott | 55/471 X |
| 3,844,741 | 10/1974 | Dimitrik | 55/279 X |
| 3,928,008 | 12/1975 | Peterson | 55/473 X |
| 3,966,442 | 6/1976 | Waters | 55/471 |

Primary Examiner—John Adee
Assistant Examiner—E. Rollins Cross
Attorney, Agent, or Firm—Vogel, Dithmar, Stotland, Stratman & Levy

[57] ABSTRACT

A dispenser for odor control agents comprising a generally cylindrical housing having air openings therein adjacent to each end thereof and including a base, a fan mounted on the base for drawing air through the openings adjacent to one end of the housing to establish an air stream through the housing, a cartridge removably mounted on the base and including a compartment for receiving an odor control agent, a duct for directing the air stream through the compartment past the odor control agent and out through the openings adjacent to the other end of the housing, a cover shiftably mounted on the base and movable between a closed position and an open position wherein the fan and the cartridge are accessible for removal and servicing, and an air controller in the path of the air stream including two apertured members shiftable so as to align the apertures to provide maximum flow of air or to place the apertures in substantial non-alignment to block the flow of air.

14 Claims, 12 Drawing Figures

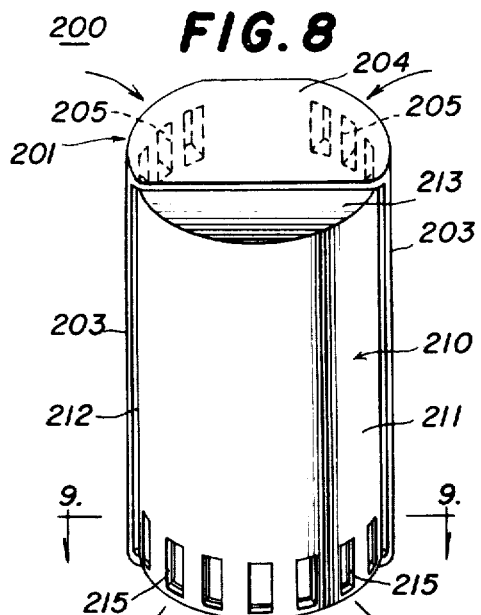
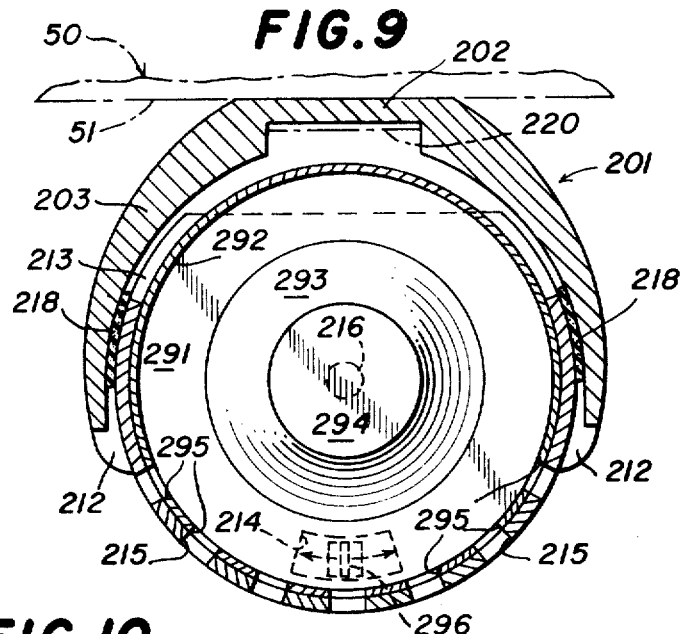
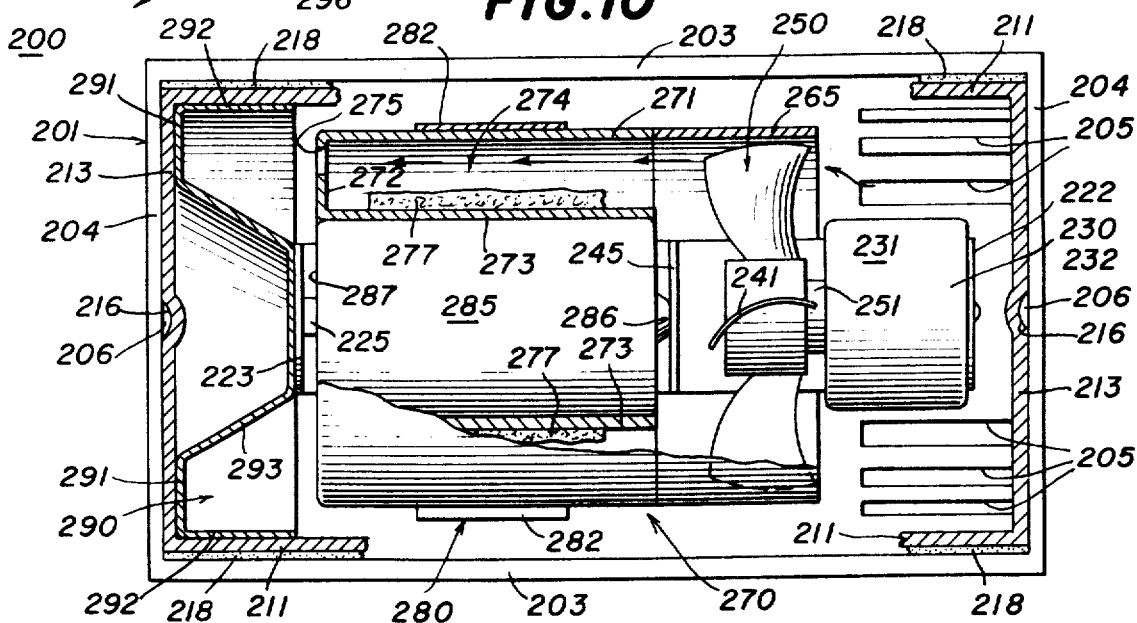
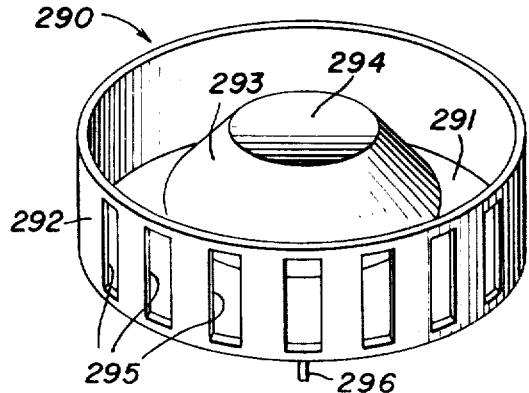
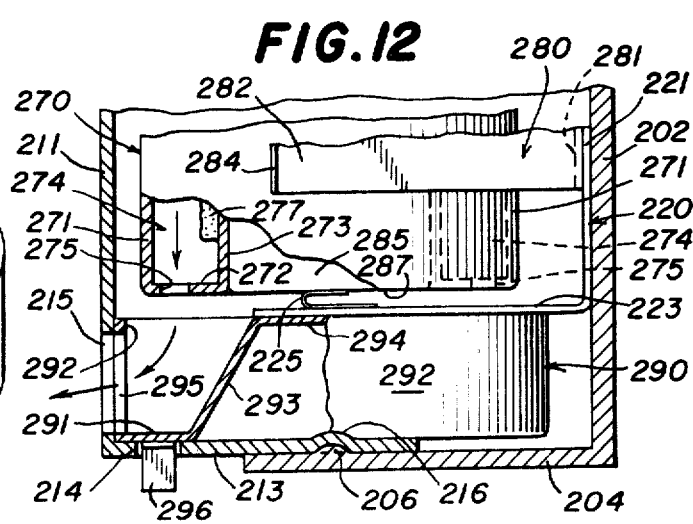

DISPENSER FOR ODOR CONTROL AGENT

BACKGROUND OF THE INVENTION

The present invention relates generally to dispensers for odor control agents or deodorants, and specifically to the provision of a dispenser wherein the cartridge containing the odor control agent and the fan for causing the air stream through the cartridge are accessible through a cover.

Certain dispensers for odor control agents heretofore have not provided ready access to the cartridge containing the odor control agent or to the fan that causes the air stream to pass across the odor control agent and out into the adjacent air space. As a result, it has not been economical to use and service these prior dispensers.

It often is desirable to place the dispenser in different positions around the room, such as, near the ceiling, or on a piece of furniture, or perhaps on the floor. Dispensers available heretofore have not been readily adapted for placement in all such positions, whereby multiplicity of dispensers had to be provided.

Finally, it has been found desirable to control the amount of air flowing through the dispenser, and thus control the amount of the odor control agent dispensed into the surrounding air. Prior dispensers have not provided for adequate air control.

SUMMARY OF THE INVENTION

The present invention provides a dispenser for odor control agents wherein the cartridge containing the odor control agent and the fan for creating the air stream thereby are readily accessible through a cover for the dispenser, and which can be used in all orientations of the housing and in all portions of a room.

This is accomplished in the present invention, and it is an object of the present invention to accomplish these desired results, by providing a dispenser for odor control agents comprising a generally cylindrical housing having air openings therein adjacent to each end thereof and including a base, a fan mounted on the base for drawing air through the openings to establish an air stream through the housing, a cartridge removably mounted on the base and including a compartment for receiving an odor control agent therein, duct means for directing the air stream of the fan through the compartment past the odor control agent therein and out through openings adjacent to the other end of the housing, and a cover for the base shiftably mounted with respect thereto for movement between a closed operating position and an open servicing position wherein the fan and the cartridge are accessible for removal and replacement and servicing, the housing and the fan and the cartridge being constructed and arranged so that the dispenser is operable in all orientations of the housing.

Another object of the invention is to provide a dispenser of the type set forth, wherein an air controller is disposed in the path of the air stream of the fan and includes a first apertured member fixedly mounted with respect to the housing and a second apertured member shiftable with respect to the housing and with respect to the first member, the members of the air controller in a first position thereof having the apertures thereof in alignment to provide for maximum flow of the air stream therethrough and the members in a second position thereof having the apertures thereof in substantial non-alignment substantially to block the flow of the air stream therethrough and the members having a plurality of intermediate positions between the first and second positions selectively to adjust the flow of the air stream therethrough.

In connection with the foregoing object, it is another object of the invention to provide a dispenser having an air controller of the type set forth wherein the first member is mounted in the end of the duct means adjacent to the air openings in the one end of the housing and the second member is mounted adjacent to the first member and shiftable with respect thereto.

Also in connection with these foregoing objects, it is another object of the invention to provide a dispenser having a controller of the type set forth wherein the cover has openings therein at the other end of the housing and the air controller has aperures cooperating with the openings in the cover for controlling the flow of air therethrough.

Further featuresof the invention pertain to the particular arrangement of the parts of the dispenser, whereby the above outlined and additional operating features thereof are attained.

The invention, both as to its organization and method of operation, together with further features and advantages thereof will best be understood with reference to the following specification taken in connection with the accompanying drawings.

BRIEF DESCRIPTION OF THE DRAWINGS

FIG. 8 is a perspective view of a second preferred embodiment of a dispenser for odor control agents, this dispenser also being made in accordance with and embodying the principles of the present invention.

FIG. 9 is an enlarged view in horizontal section along the line 9—9 of FIG. 8;

FIG. 10 is a view in horizontal section through the dispenser of FIG. 8 with certain portions broken away;

FIG. 11 is a perspective view of the air controller forming a part of the dispenser of FIGS. 8 to 10; and FIG. 12 is a fragmentary view in vertical section through the lower portions of the dispenser of FIGS. 8 to 10.

DESCRIPTION OF THE PREFERRED EMBODIMENTS

Figure 1:
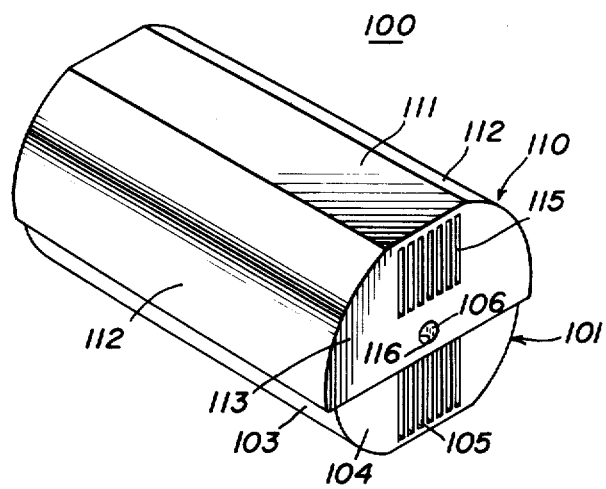
FIG. 1 is a perspective view of a first preferred embodiment of a dispenser for odor control agents, which dispenser is made in accordance with and embodies the principles of the present invention.

There is illustrated in FIGS. 1 to 7 of the drawings a first preferred embodiment of a dispenser 100 made in accordance with and embodying the principles of the present invention and particularly adapted to dispense odor control agents into a room, or the like. The dispenser 100 is generally cylindrical in shape and has a housing formed from a base 101 and a cover 110 that is shiftable with respect to the base 101. The base 101 more particularly has a flat rear wall 102 that can be conveniently used to position the dispenser 100 upon a flat surface as is illustrated in FIG. 1. Integral with and extending upwardly from the longitudinal edges of the flat rear wall 102 are curved side walls 103, the ends of the side walls 103 being closed by end walls 104. Air to be passed through the dispenser 100 is admitted to the interior of the housing through a first set of slots 105 in the end of the base 101 visible in FIG. 1. Adjacent to the slots 105 is a post 106 integral with the adjacent wall 104 and extending outwardly therefrom and in essentially the geometric center of the cylindrical housing for the dispenser 100. It will be noted that air openings or slots 105 are also provided in the other end of the base 101 (see FIG. 3) and a second post 106 is also provided adjacent to those slots 105.

Figure 2:
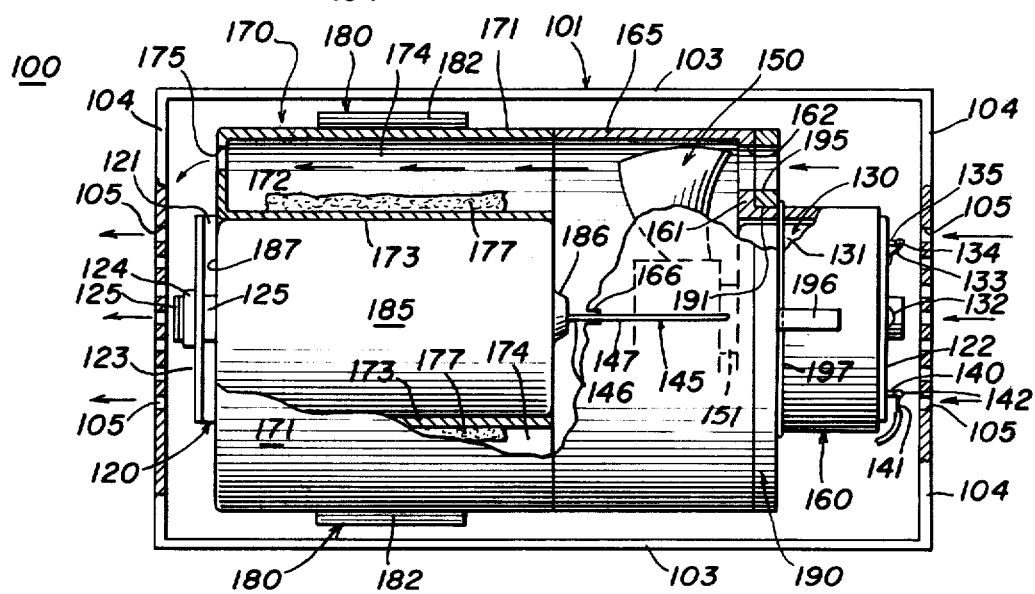
FIG. 2 is a view in longitudinal section on an enlarged scale through the dispenser of FIG. 1, with certain portions broken away.
Figure 3:
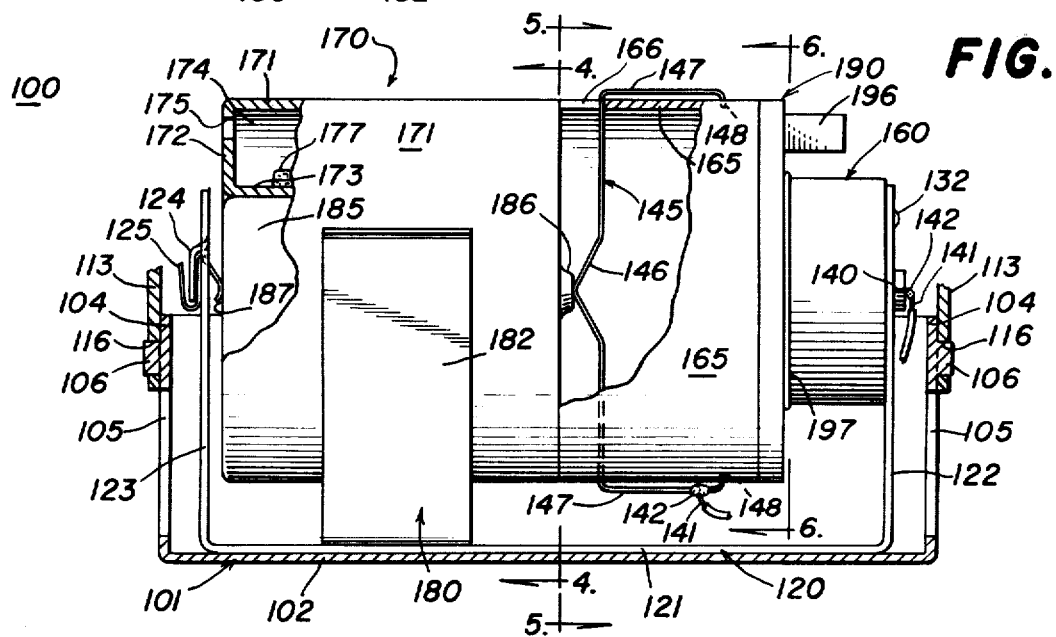
FIG. 3 is a view in longitudinal section taken at right angles to the view of FIG. 2 and also with certain portions broken away.
Figure 4:
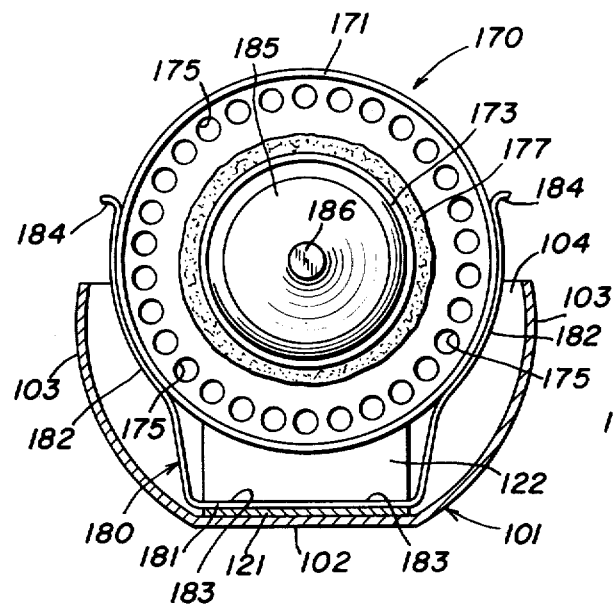
FIG. 4 is a fragmentary view in cross section along the line 4—4 of FIG. 3.
Figure 5:
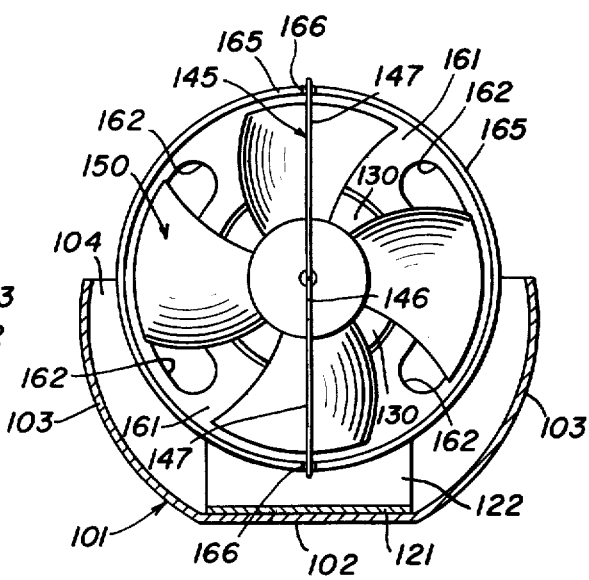
FIG. 5 is a fragmentary view in vertical section along the line of 5—5 of FIG. 3.

The cover 110 that cooperates with the base 101 to provide the essentially cylindrical housing for the dispenser 100 also is provided with a flat front wall 111 which upon occasion can be utilized to position the dispenser 100 if desired. Integral with the longitudinally extending edges of the front wall 111 are two curved side walls 112, the ends of the side walls 112 being closed by end walls 113. Each of the end walls 113 has slots 115 therein and adjacent to the slots 115 are openings 116, respectively, that receive the posts 106 therethrough. In this manner the base 101 and the cover 110 are pivotably interconnected about the axes of the posts 106. It will be seen that the cover 110 extends over and receives therein the base 101 so that the cover 110 can be shifted or pivoted with respect to the base 101 to expose the interior of the base 101, all as will be explained more fully hereinafter. The slots 105 and the slots 115 at the end of the dispenser 100 to the right in FIGS. 1 to 3 provide the inlet for air into the dispenser 100, while the slots 105 and 115 in the end of the dispenser 100 to the left in FIGS. 1 to 3 provide an exit for the air drawn into the dispenser 100.

Disposed within the base 101 and suitably secured thereto is a mounting bracket 120 that is essentially U-shaped and includes a longitudinally extending attachment portion 121 secured to the wall 102 and terminating at points spaced inwardly from the end walls 104 and carrying on the opposite ends thereof a motor mounting flange 122 and a battery contacting flange 123. The flange 123 has a finger 124 struck therefrom and extending outwardly and carrying an electrical contact 125 forming a part of the electrical circuit to be described more fully hereinafter.

The flange 122 carries a motor 130 which is battery operated, as illustrated, and includes a housing 131 (see FIG. 2), a fastener 132 securing the motor housing 131 to the flange 122. Two electrical terminals 135 and 140 are provided for the motor 130, the terminal 135 being connected by a conductor 133 to the flange 122, solder connections 134 being provided as required. In this manner the terminal 135 is connected via the mounting bracket 120 to the electrical contact 125. The terminal 140 is connected by a conductor 141 to a contact clip 145, solder connections 142 being made where required. The contact clip 145 has a central V portion that carries on the opposite end thereof L-shaped ends 147 terminating in fingers 148 that hold the contact clip in operative position, all as will be discussed hereinafter.

Surrounding the motor 130 is a shroud 160 and integral with one end of the shroud 160 is a laterally outwardly extending flange 161 having a generally cylindrical periphery and carrying thereon a cylindrical duct 165 that extends from the motor 130 towards the opposite end of the dispenser 100. Disposed within the duct 165 is a fan 150 connected to the motor 130 by a suitable shaft 151, whereby the motor 130 serves to drive the fan 150 within the cylindrical duct 165. The fan 150 when operated serves to pull air from the right in the direction of the arrows through the openings 105 and 115 and through two arcuate or crescent-shaped openings 162 in the flange 161 (see FIG. 7) and thus into the interior of the duct 165.

Also mounted in the dispenser 100 is a cartridge 170 which has an outer cylindrical wall 171 in general longitudinal alignment with the duct 165 and an end wall 172 having an opening centrally therein that is surrounded by an inner cylindrical wall 173 that extends back toward the duct 165. The walls 171, 172 and 173 cooperate to form therein an annular compartment 174 which is provided with a plurality of circular openings 175 in the end wall 172 to permit passage of air into, through and out of the compartment 174. Disposed within the compartment 174 is a source of odor control agent, such as a deodorant carrier 177. The carrier 177 may be a porous plastic, a gel or a wick carrying liquid, or some other control agent. The carrier 177 may contain a material that can be vaporized into the air stream passing thereby thus to effect and change the odor of the air stream, or the carrier 177 may comprise absorbent material which will remove from the air stream passing thereby undesirable odor forming materials.

In order to hold the cartridge 170 in the desired position within the dispenser 100, a mounting clip 180 has been provided (see particularly FIG. 4), the mounting clip 180 including an attachment portion 181 that is secured such as by fasteners 183 to the mounting bracket 120 and in turn to the base 101. Integral with the attachment portion 181 are resilient arms 182 that releasably engage and secure the cartridge 170. Preferably the outer ends of the arms 182 are outturned as at 184 so as to facilitate the mounting and removal of the cartridge 170 with respect to the mounting clip 180.

Disposed within the inner cylindrical wall 173 is a battery 185 for providing energy to drive the motor 130, the battery 185 having a first terminal 186 disposed to the right in FIG. 2 and having a second terminal 187 disposed to the left in FIG. 2. The terminal 186 is connected via the contact clip 145 and the conductor 141 to the motor terminal 135. It is pointed out that the arms 147 of the clip 145 pass through slots 166 in the duct 165 and that the fingers 148 are disposed in openings in the duct 165 so as firmly to mount clip 145 on the duct 165 and thus to maintain it in operative relation with respect to the battery terminal 186. The second battery terminal 187 is contacted by the electrical contact 125 carried by the mounting bracket 120, whereby the electrical connection is made from the second battery terminal 187 via the electrical contact 125, the mounting bracket 120 and the conductor 133 to the other motor terminal 135.

An air flow controller 190 is provided to control the flow of air through the air duct 165 and the cartridge 170. As illustrated, the flow controller 190 is in the form of a cylindrical disc having an aperture 191 therein that receives therethrough the motor shroud 160, whereby the controller 190 can rotate about and is supported by the motor shroud 160. Formed in the controller 190 are two crescent-shaped openings 195 which have the same size as and are arranged equiangularly around the controller 190 to match the crescent-shaped openings 162 in the flange 161 (see FIGS. 6 and 7). There further is provided on the controller 190 a handle 196 that extends to the right as viewed in FIGS. 2 and 3 and is readily accessible to a user when the housing cover 110 is moved to the open position. Finally, there is provided a retainer 197 that is in the form of a metal band fitting in a groove in the shroud 160 and bearing against the adjacent surface of the flow controller 190 disposed to the right of FIGS. 2 and 3 to hold the controller 190 in operative position with respect to the shround flange 161.

Figure 6:
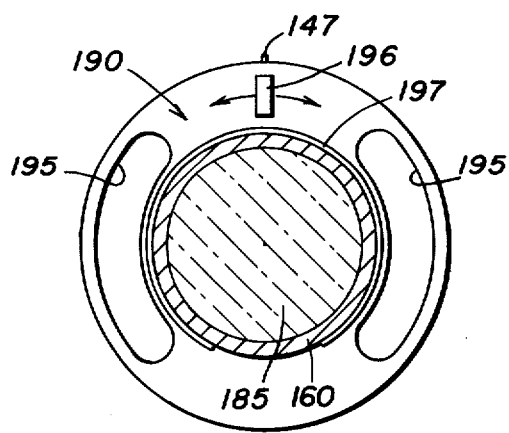
FIG. 6 is a view in section along the line 6—6 of FIG. 3 showing the air controller in a position wherein the air stream therethrough is substantially unhindered providing maximum air flow.

In a first position of the controller 190 with respect to the flange 161 illustrated in FIG. 6, the crescent-shaped openings 162 and 195 therein are in alignment, these openings being of the same size and the same shape and being spaced apart equiangularly the same distance, so that in this first position of the parts, there is a maximum combined opening provided for the flow of air therethrough. Accordingly, when the motor 130 is energized by the battery 185, the fan 150 is operated to draw air through the slots 105 and 115 to the right in FIGS. 1 to 3 and then through the aligned openings 162 and 195 in the flange 161 and the controller 190 respectively, and then through the compartment 174 of the cartridge 170 and out of the openings 175 and finally from the dispenser 100 through the slots 105 and 115 to the left in FIGS. 1 to 3. The air stream thus established flows at a maximum rate through the compartment 174 and past the carrier 177, whereby the maximum effect upon the odor of the air stream is obtained.

Figure 7:
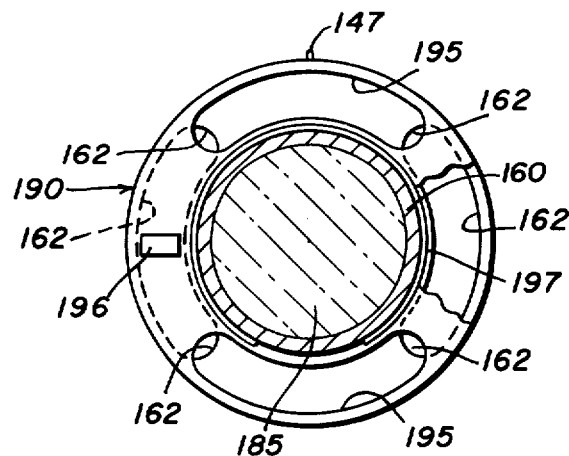
FIG. 7 is a view similar to FIG. 6 showing the air controller in a second position essentially blocking the flow of air therethrough.

In a second position of the flow controller 190 with respect to the flange 161 illustrated in FIG. 7, the crescent-shaped openings 162 and 195 are in substantial non-alignment (see FIG. 7) so that only a very small overlapping portion thereof provides a passage for air flow therethrough, whereby there is a substantial blockage of the air stream through the dispenser 100 and past the deodorant carrier 177. It will be appreciated that by using the handle 196, any desired adjusted position between those illustrated in FIGS. 6 and 7 can be achieved, thereby to adjust to any desired degree the flow of air through the dispenser 100 and past the deodorant carrier 177.

Since the dispenser 100 is entirely self-contained, it may be positioned in any orientation as required. If it is placed upon a generally horizontal support surface in the position illustrated in FIG. 1, then the air stream will be laterally therethrough and can be directed in any horizontal direction desired by the user. The dispenser 100 can also be operated with the longitudinal axis thereof directed vertically, and with the motor either positioned up or down. Accordingly, if the dispenser 100 is placed high on a wall, the air stream can be directed downwardly by placing the motor 130 upwardly. Likewise if the dispenser 100 is placed near the floor, then it is desired that the air stream be directed upwardly, in which case the motor 130 is disposed downwardly.

Summarizing, the dispenser 100 can be placed in any orientation of its longitudinal axis, and the air stream therethrough can be adjusted by means of the controller 190 to any desired degree. The cover 110 can be pivoted with respect to the base 101 to expose the entire interior of the dispenser 100 for ease in service and replacement of parts as required.

In FIGS. 8 to 12 of the drawings there is illustrated a second preferred embodiment of a dispenser 200 made in accordance with and embodying the principles of the present invention. Many of the parts of the dispenser 200 are constructed and operate like parts of the dispenser 100 and accordingly parts of the dispenser 200 have had reference numerals applied thereto in the 200 series that correspond to like numbered parts in the 100 series as applied to the dispenser 100. The dispenser 200 is generally cylindrical in shape and has a housing formed from a base 201 and a cover 210 that is shiftable with respect to the base 201. The base 201 has a construction best illustrated in FIG. 9 and includes a rear wall 202 that may be suitably secured to an upstanding support wall 50, and more particularly on the surface 51 thereof. Integral with and extending outwardly from the longitudinal edges of the rear flat wall 202 are curved side walls 203, the ends of the side walls 203 being closed by end walls 204. The base 201 is essentially semi-cylindrical in shape and has rectangular openings or slots 205 in the side walls 203 thereof for the admission of air to be treated.

Again referring to FIG. 9, the cover 210 is part-cylindrical in shape and includes a main wall 211 which fits within the inner surfaces of the base side walls 203 and is preferably held in position by a pair of stop members 212 secured to the base side walls 203 and cooperating therewith to surround more than 50% of the circumstance defined by the outer surface of the cover main wall 211, so as to maintain the cover 210 in operative relationship with the base 201, as will be explained more fully hereinafter. The cover 210 is provided at each end with end walls 213 which are generally circular in shape and extend beyond the rear edges of the main wall 211 but are cut off as is illustrated toward the top of FIG. 9. The lowermost end of the cover 210 is provided with a plurality of rectangular slots 215 for passage of air from the dispenser 200 and the lowermost end wall 213 as seen in FIGS. 9 and 12 is provided with a crescent-shaped opening 214 to receive the handle of an air controller to be more fully described hereinafter. In order removably to mount the cover 210 upon the base 201, the base end walls 204 are provided with part spherical bumps 206 on the inner surfaces thereof in alignment with the longitudinal axis of rotation of the cover 210, and the end walls 213 of the cover 210 have complementarily shaped recesses 216 therein thus to trap the cover 210 upon the base 201. It will be appreciated that the side walls 203 and the end walls 204 of the base 201 are slightly resilient and can be spread apart to permit the insertion and removal of the cover 210 with respect to the base 201. There further are provided two bearing strips 218 interposed between the adjacent surfaces of the base side walls 203 and the cover main wall 211 to provide for a resilient cushioning therebetween and to block the passage of air through the space therebetween.

As a result of the above described construction of the base 201 and the cover 210, the cover 210 can be manually rotated about the bearings formed by the bumps 206 and the recesses 216 so as to expose the interior of the dispenser 200 for service and maintenance as will be described more fully hereinafter. The slots 205 in the base 201 and the slots 215 in the cover 210 provide inlets and outlets, respectively, for air passing through the dispenser 200.

Disposed within the base 201 and suitably secured thereto is a mounting bracket 220 that is essentially U-shaped and includes a longitudinally extending attachment portion 221 secured to the wall 202 and terminating at points based inwardly from the end walls 204 and carrying on the opposite ends thereof a motor mounting flange 222 and a battery contacting flange 223. The flange 223 carries an electrical contact 225 forming a part of the electrical circuit to be discussed more fully hereinafter. The flange 222 carries a motor 230 which is battery operated, as illustrated, and includes a housing 231 (see FIG. 10). A fastener 232 secures the motor housing 231 to the flange 222, and the flange 222 is further electrically connected to one of the electrical terminals provided for the motor 230. This motor terminal more particularly is connected via the mounting bracket 220 to the electrical contact 225 which is in contact with one of the battery terminals to be described later. The motor 230 drives a fan 250 connected thereto by a suitable shaft 251, the fan being arranged to draw air longitudinally through the dispenser 200. Surrounding the fan 250 is a fixed air duct 265 cylindrical in shape and secured to the mounting bracket 220. The fan 250 when operated serves to pull air from the right in FIG. 10 through the slots 205 and into the duct 265.

Also mounted in the dispenser 200 is a cartridge 270 which has an outer cylindrical wall 271 in general longitudinal alignment with the duct 265 and an end wall 272 having an opening center thereof which is surrounded by an inner cylindrical wall 273 that extends back towards the duct 265. The walls 271, 272 and 273 cooperate to form therein an annular compartment 274 which is provided with circular openings 275 in the end wall 272 to permit passage of air into, through and out of the compartment 274. Disposed within the compartment 274 is a source of odor control agent, such as a deodorant carrier 277 which may be of the same type as the deodorant carrier 177 described above with respect to the dispenser 100.

In order to hold the cartridge 270 in the desired position within the dispenser 200, a mounting clip 280 has been provided (see particularly FIGS. 10 and 12), the mounting clip 280 including an attachment portion 281 that is secured such as by suitable fasteners to the mounting bracket 220 and in turn to the base 201. Integral with the attachment portion 281 are resilient arms 282 that releasably engage and secure the cartridge 270. Preferably the outer ends of the arms 282 are outturned as at 284 (see FIG. 12) so as to facilitate the mounting and removal of the cartridge 270 with respect to the mounting clip 280.

Disposed within the inner cylindrical wall 273 is a battery 285 for providing energy to drive the motor 230, the battery 285 having a first terminal 286 disposed to the right in FIG. 10 and having a second terminal 287 disposed to the left in FIG. 10. The terminal 286 is connected via a contact clip 245 and a conductor 241 to the second motor terminal. The second battery terminal 287 is connected by the electrical contact 225 carried by the mounting brackets 220, whereby the electrical connection is made from the second battery terminal 287 via the electrical contact 225, the mounting bracket 220 and the flange 222 to the first motor terminal.

An air flow controller 290 is provided to control the flow of air from the housing of the dispenser 200, and particularly through the air exit openings or slots 215 in the lower end of the cover 210. As illustrated, the flow controller 290 is in the form of a flat bottom wall 291 circular in outline and having a cylindrical flange or side wall 292 extending therearound. Disposed centrally of the bottom 201 is an upstanding conical bearing 293 extending therefrom in the same direction as the side wall 292 and having a flat bearing surface 294 in the upper end thereof that is adapted to bear against the flange 223 of the mounting bracket 220. Formed in the side wall 292 is a plurality of elongated essentially rectangular openings or slots 295 that are shaped identical to the slots 215 in the cover 210 and are equiangularly spaced therealong the same distance as are the slots 215. There further is provided on the controller and extending downwardly therefrom a handle 296 which extends through the crescent-shaped opening 214 described above in the end wall 213 of the cover 210, whereby the handle 296 is readily accessible to a user even with the housing cover 210 in the closed position thereof.

From the above described construction of the parts, it will be appreciated that the controller 211 fits nicely within the lower end of the housing cover 210 and is rotatable about the central axis thereof. Rotation of the flow controller 290 with respect to the cover 210 serves to move the slots 295 with respect to the slots 215. At a first position of the controller 290 with respect to the cover 210, the slots 215 and 295 are in alignment (as illustrated in FIG. 12). Inasmuch as the slots 215 and 295 are the same shape and are spaced apart equiangularly the same distance, the slots in the first position provide a maximum opening for flow of air therethrough. Accordingly, when the motor 230 is energized by the battery 285, the fan 250 is operated to draw air through the slots 215 in the upper end of the base 201 as illustrated in FIG. 8, then through the compartment 274 of the cartridge 270 and out through the aligned openings 215 and 295 in the lower portion of the housing cover 210 as illustrated in FIGS. 8 and 12. The air stream thus established flows at a maximum rate through the compartment 274 and past the carrier 277, whereby the maximum effect upon the odor of the air stream is obtained.

In a second position of the flow controller 290 with respect to the housing cover 210, the slots 215 and 295 are in substantial non-alignment, so as substantially to block passage of air therethrough, whereby there is a substantial blockage of the air stream through the dispenser 200 and past the carrier 277. It will be appreciated that by using the handle 296, any adjusted position between maximum flow and minimum flow can be achieved, thereby to adjust to any desired degree the flow of air through the dispenser 200 and past the deodorant carrier 277.

The dispenser 200, like the dispenser 100 described above, is entirely self-contained, and may be positioned in any orientation as required. The cover 210 may be pivoted with respect to the base 101 to expose the entire interior of the dispenser 200 for ease in service and replacement of parts as required. The dispenser 100 and 200 also are small in size, and may typically have a 3 inch overall diameter and a 5 inch overall length. A preferred material of construction for the bases 101 and 201, the covers 110 and 210, the ducts 165 and 265, the cartridges 180 and 280, and the controllers 190 and 290 is a suitable plastic.

While there has been described what is at present considered to be the preferred embodiments of the invention, it will be understood that various modifications may be made therein, and it is intended to cover in the appended claims all such modifications as fall within the true spirit and scope of the invention.

What is claimed is:

1. A dispenser for odor control agents comprising a housing having air intake openings and air discharge openings therein and including a base, a fan mounted on said base for drawing air through said air intake openings to establish an air stream through said housing, a cartridge removably mounted on said base and including a compartment for receiving an odor control agent therein, duct means for directing the air stream of said fan through said compartment past the odor control agent therein and out through the air discharge openings, and a cover for said base shiftably mounted with respect thereto for movement while mounted between a closed operating position and an open servicing position, said cover in the closed position thereof cooperating with said base to enclose said fan and said cartridge, said cover in the open position thereof rendering said fan and said cartridge accessible for removal and replacement and servicing, said housing and said fan and said cartridge being constructed and arranged so that the dispenser is operable in all orientations of said housing.

2. The dispenser set forth in claim 1, wherein said base is part-cylindrical in shape with end walls, and at least a portion of said openings are in said base.

3. The dispenser set forth in claim 1, wherein said base is part-cylindrical in shape with end walls, and said air intake openings are in said base in the part-cylindrical portion thereof adjacent to one of said end walls, and said air discharge openings are in said cover.

4. The dispenser set forth in claim 1, wherein the power source for said fan is a battery mounted in said cartridge.

5. The dispenser set forth in claim 1, wherein a portion of said duct means is mounted on said base and surrounds said fan.

6. The dispenser set forth in claim 1, wherein a portion of said duct means is on said cartridge.

7. The dispenser set forth in claim 1, and further comprising a resilient mounting clip mounted on said base and removably holding said cartridge in said housing.

8. The dispenser set forth in claim 1, wherein said cover is pivotally mounted on said base.

9. A dispenser for odor control agents comprising a housing having air intake openings and air discharge openings therein and including a base, a fan mounted on said base for drawing air through said air intake openings to establish and air stream through said housing, a cartridge removably mounted on said base and including a compartment for receiving an odor control agent therein, duct means for directing the air stream of said fan through said compartment past the odor control agent therein and out through said air discharge openings, a cover for said base shiftably mounted with respect thereto for movement while mounted between a closed operating position and an open servicing position, said cover in the closed position thereof cooperating with said base to enclose said fan and said cartridge, said cover in the open position thereof rendering said fan and said cartridge accessible for removal and replacement and servicing, and an air controller disposed in the path of the air stream of said fan and including a first apertured member fixedly mounted with respect to said housing and a second apertured member shiftable with respect to said housing and with respect to said first member, said members of said air controller in a first position thereof having the apertures thereof in alignment to provide for maximum flow of the air stream therethrough and said members in a second position thereof having the apertures thereof in substantial non-alignment substantially to block the flow of the air stream therethrough and said members having a plurality of intermediate positions between the first and second positions selectively to adjust the flow of the air stream therethrough, said housing and said fan and said cartridge and said air controller being constructed and arranged so that the dispenser is operable in all orientations of said housing.

10. The dispenser set forth in claim 9, and further comprising a handle connected to said second member of said air controller for adjusting said members among the several positions thereof.

11. A dispenser for odor control agents comprising a housing having air intake openings and air discharge openings therein and including a base, a fan mounted on said base for drawing air through said air intake openings to establish an air stream through said housing, a cartridge removably mounted on said base and including a compartment for receiving an odor control agent therein, duct means for directing the air stream of said fan through said compartment past the odor control agent therein and out through said air discharge openings, a cover for said base shiftably mounted with respect thereto for movement while mounted between a closed operating position and an open servicing position, said cover in the closed position thereof cooperating with said base to enclose said fan and said cartridge, said cover in the open position thereof rendering said fan and said cartridge accessible for removal and replacement and servicing, and an air controller disposed in the path of flow of the air stream of said fan and including a first member having apertures therein and disposed in the end of said duct means adjacent to the air intake openings in said housing and a second member having apertures therein and mounted adjacent to said first member and shiftable with respect thereto, said members of said air controller in a first position thereof having the apertures thereof in alignment to provide for maximum flow of the air stream therethrough and said members in a second position thereof having the apertures thereof in substantial non-alignment substantially to block the flow of the air stream therethrough and said members having a plurality of intermediate positions between said first and second positions selectively to adjust the flow of the air stream therethrough, said housing and said fan and said cartridge and said air controller being constructed and arranged so that the deodorant dispenser is operable in all orientations of said housing.

12. The dispenser set forth in claim 11, and further comprising a handle on said second member extending therefrom and engageable by a user when said cover is in the open position thereof.

13. A dispenser for odor control agents comprising a housing having air intake openings and air discharge openings therein and including a base, a fan mounted on said base for drawing air through said air intake openings to establish an air stream through said housing, a cartridge removably mounted on said base and including a compartment for receiving an odor control agent therein, duct means for directing the air stream of said fan through said compartment past the odor control agent therein and out through said air discharge openings, a cover for said base shiftably mounted with respect thereto for movement while mounted between a closed operating position and an open servicing position, said cover in the closed position thereof cooperating with said base to enclose said fan and said cartridge, said cover in the open position thereof rendering said fan and said cartridge accessible for removal and replacement and servicing, and an air controller disposed in the path of the air stream of said fan, said cover and said air controller having apertures therein such that when said air controller is in a first position thereof said apertures are in alignment to provide for maximum flow of the air stream therethrough and such that when said air controller is in a second position thereof said apertures are in substantial non-alignment substantially to block the flow of the air stream therethrough and such that when said air controller is in one of a plaurality of intermediate positions between said first and second positions said apertures are in partial alignment to adjust the flow of the air stream of said fan therethrough, said housing and said fan and said cartridge and said air controller being constructed and arranged so that the deodorant dispenser is operable in all orientations of said housing.

14. The dispenser set forth in claim 13, and further comprising a handle on said air controller extending through said housing and accessible to a user for adjusting the position of said air controller and thus to adjust the flow of the air stream of said fan.

* * * * *